(12) United States Patent
Knoop et al.

(10) Patent No.: US 11,037,657 B2
(45) Date of Patent: *Jun. 15, 2021

(54) PERSONALIZED QUESTIONNAIRE FOR HEALTH RISK ASSESSMENT

(71) Applicant: International Business Machines Corporation, Armonk, NY (US)

(72) Inventors: Sarah E. Knoop, San Jose, CA (US); Tan Hung Marie Ng, San Jose, CA (US); John T. E. Timm, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 562 days.

This patent is subject to a terminal disclaimer.

(21) Appl. No.: 15/716,819

(22) Filed: Sep. 27, 2017

(65) Prior Publication Data

US 2019/0095590 A1    Mar. 28, 2019

(51) Int. Cl.
*G16H 10/20* (2018.01)
*G16H 50/30* (2018.01)
(Continued)

(52) U.S. Cl.
CPC ............ *G16H 10/20* (2018.01); *G16H 10/60* (2018.01); *G16H 15/00* (2018.01); *G16H 20/00* (2018.01);
(Continued)

(58) Field of Classification Search
None
See application file for complete search history.

(56) References Cited

U.S. PATENT DOCUMENTS

| 7,092,821 B2 * | 8/2006 | Mizrahi ................. A63F 13/10 702/1 |
| 8,275,803 B2 | 9/2012 | Brown et al. |

(Continued)

FOREIGN PATENT DOCUMENTS

WO    WO 2013/054241 A1    4/2013

OTHER PUBLICATIONS

List of IBM Patents or Patent Applications Treated as Related, Dec. 13, 2017, 2 pages.
(Continued)

*Primary Examiner* — Michael Tomaszewski
*Assistant Examiner* — Jay M. Patel
(74) *Attorney, Agent, or Firm* — Francis Lammes; Stephen J. Walder, Jr.; Ryan G. Lewis

(57) ABSTRACT

A mechanism is provided to implement a health risk assessment system for adaptively and dynamically generating a personalized questionnaire for health risk assessment of a patient. A set of responses are analyzed and a patient is grouped to an initial group that matches a similar patient group. Utilizing the initial group, an initial question is selected to present to the patient. Responsive to receiving a current response to the initial question, the current response is analyzed, the patient is grouped to a next group, and a next question is identified and presented to the patient. The process continues until a last group is reached where a scoring of possible health risks associated with the patient is performed based on each response provided by the patient and identified groupings. A final possible health risk or ranked set of possible health risks is then presented based on the scoring.

12 Claims, 4 Drawing Sheets

(51) Int. Cl.
*G16H 50/20* (2018.01)
*G16H 10/60* (2018.01)
*G16H 20/00* (2018.01)
*G16H 70/20* (2018.01)
*G16H 40/67* (2018.01)
*G16H 50/50* (2018.01)
*G16H 15/00* (2018.01)
*G16H 80/00* (2018.01)

(52) U.S. Cl.
CPC .............. *G16H 40/67* (2018.01); *G16H 50/20* (2018.01); *G16H 50/30* (2018.01); *G16H 50/50* (2018.01); *G16H 70/20* (2018.01); *G16H 80/00* (2018.01)

(56) References Cited

U.S. PATENT DOCUMENTS

| | | | |
|---|---|---|---|
| 8,311,849 B2 | 11/2012 | Soto et al. | |
| 8,478,769 B2 | 7/2013 | Goldfarb | |
| 9,401,881 B2 | 7/2016 | Isensee et al. | |
| 2006/0218007 A1* | 9/2006 | Bjorner | G06Q 10/10 |
| | | | 705/2 |
| 2008/0065471 A1* | 3/2008 | Reynolds | G06Q 30/0203 |
| | | | 705/7.32 |
| 2009/0216558 A1 | 8/2009 | Reisman et al. | |
| 2009/0240529 A1 | 9/2009 | Chess et al. | |
| 2009/0287678 A1 | 11/2009 | Brown et al. | |
| 2011/0066587 A1 | 3/2011 | Ferrucci et al. | |
| 2011/0125734 A1 | 5/2011 | Duboue et al. | |
| 2011/0276507 A1* | 11/2011 | O'Malley | G06Q 30/00 |
| | | | 705/321 |
| 2012/0065999 A1* | 3/2012 | Takatoku | G06F 19/3456 |
| | | | 705/3 |
| 2013/0007055 A1 | 1/2013 | Brown et al. | |
| 2013/0018652 A1 | 1/2013 | Ferrucci et al. | |
| 2013/0066886 A1 | 3/2013 | Bagchi et al. | |
| 2013/0073344 A1* | 3/2013 | Parent | G06Q 10/06 |
| | | | 705/7.39 |
| 2013/0116578 A1* | 5/2013 | An | A61B 5/4842 |
| | | | 600/484 |
| 2013/0144645 A1* | 6/2013 | Bjorner | G06Q 30/00 |
| | | | 705/2 |
| 2014/0046682 A1* | 2/2014 | Soto | G16H 10/20 |
| | | | 705/2 |
| 2014/0114680 A1* | 4/2014 | Mills | G16H 50/30 |
| | | | 705/2 |
| 2015/0262498 A1* | 9/2015 | Wicka | G16H 40/63 |
| | | | 705/14.27 |
| 2015/0302436 A1* | 10/2015 | Reynolds | G06Q 30/0201 |
| | | | 705/7.32 |
| 2015/0326625 A1* | 11/2015 | Rosenberg | H04L 65/403 |
| | | | 715/753 |
| 2016/0004831 A1* | 1/2016 | Carlson | G16H 10/20 |
| | | | 705/2 |
| 2017/0000422 A1* | 1/2017 | Moturu | A61B 5/4836 |
| 2017/0262609 A1* | 9/2017 | Perlroth | G16H 50/30 |
| 2017/0308671 A1* | 10/2017 | Bahrami | G16H 10/60 |
| 2018/0189457 A1* | 7/2018 | Plummer | G16H 50/20 |
| 2018/0189691 A1* | 7/2018 | Oehrle | G06Q 10/063 |

OTHER PUBLICATIONS

"Comparing group e ects in risk of adverse healthcare events using Bayesian Hierarchical Model", Disclosed Anonymously, an ip.com Prior Art Database Technical Disclosure, ip.com No. IPCOM000244978D, Feb. 4, 2015, 7 pages.

"Comprehensive Continuous Risk Assessment Process", Disclosed Anonymously, an ip.com Prior Art Database Technical Disclosure, ip.com No. IPCOM000158836D, Oct. 1, 2007, 16 pages.

Goetzel, Ron Z. et al., "A Framework for Patient-Centered Health Risk Assessments: Providing Health Promotion and Disease Prevention Services to Medicare Beneficiaries", US Department of Health and Human Services, Centers for Disease Control and Prevention, https://www.cdc.gov/policy/hst/hra/frameworkforhra.pdf, (month unknown) 2011, 52 pages.

High, Rob, "The Era of Cognitive Systems: An Inside Look at IBM Watson and How it Works", IBM Corporation, Redbooks, Dec. 12, 2012, 16 pages.

McCord, M.C. et al., "Deep parsing in Watson", IBM J. Res. & Dev. vol. 56 No. 3/4 Paper 3, May/Jul. 2012, pp. 3:1-3:15.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

PERSONALIZED QUESTIONNAIRE FOR HEALTH RISK ASSESSMENT

BACKGROUND

The present application relates generally to an improved data processing apparatus and method and more specifically to mechanisms for adaptively and dynamically generating a personalized questionnaire for health risk assessment of a patient.

With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating Question and Answer (QA) systems which may take an input question, analyze it, and return results indicative of the most probable answer to the input question. QA systems provide automated mechanisms for searching through large sets of sources of content, e.g., electronic documents, and analyze them with regard to an input question to determine an answer to the question and a confidence measure as to how accurate an answer is for answering the input question.

Examples, of QA systems are Siri® from Apple®, Cortana® from Microsoft®, and question answering pipeline of the IBM Watson™ cognitive system available from International Business Machines (IBM®) Corporation of Armonk, N.Y. The IBM Watson™ system is an application of advanced natural language processing, information retrieval, knowledge representation and reasoning, and machine learning technologies to the field of open domain question answering. The IBM Watson™ system is built on IBM's DeepQA™ technology used for hypothesis generation, massive evidence gathering, analysis, and scoring. DeepQA™ takes an input question, analyzes it, decomposes the question into constituent parts, generates one or more hypothesis based on the decomposed question and results of a primary search of answer sources, performs hypothesis and evidence scoring based on a retrieval of evidence from evidence sources, performs synthesis of the one or more hypothesis, and based on trained models, performs a final merging and ranking to output an answer to the input question along with a confidence measure.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system, is provided for adaptively and dynamically generating a personalized questionnaire for health risk assessment of a patient via a health risk assessment system. The illustrative embodiment analyzes the set of responses and groups the patient to an initial group that matches a similar patient group in response to receiving a set of responses from patient and/or monitoring device associated with the patient. The illustrative embodiment utilizes the initial group to determine an initial question from a questions database to present to the patient. The illustrative embodiment, responsive to presenting the initial question to the patient and receiving a current response from the patient, analyzes the current response, groups the patient to an next group that matches a next most similar patient group, and identifies a next question from the questions database to present to the patient. The illustrative embodiment presents each of a set of next questions to the patient one by one until a last group is reached, wherein, responsive to receiving a response to each next question in the set of next questions includes analyzing the response, grouping the patient to the next group that matches the next most similar patient group, and identifying the next question from the set of questions. The illustrative embodiment performs a scoring of possible health risks associated with the patient based on each response provided by the patient and identified groupings in response to the last group being reached. The illustrative embodiment then presents the final possible health risk or ranked set of possible health risks based on the scoring to one or more of the patient or a health care professional.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
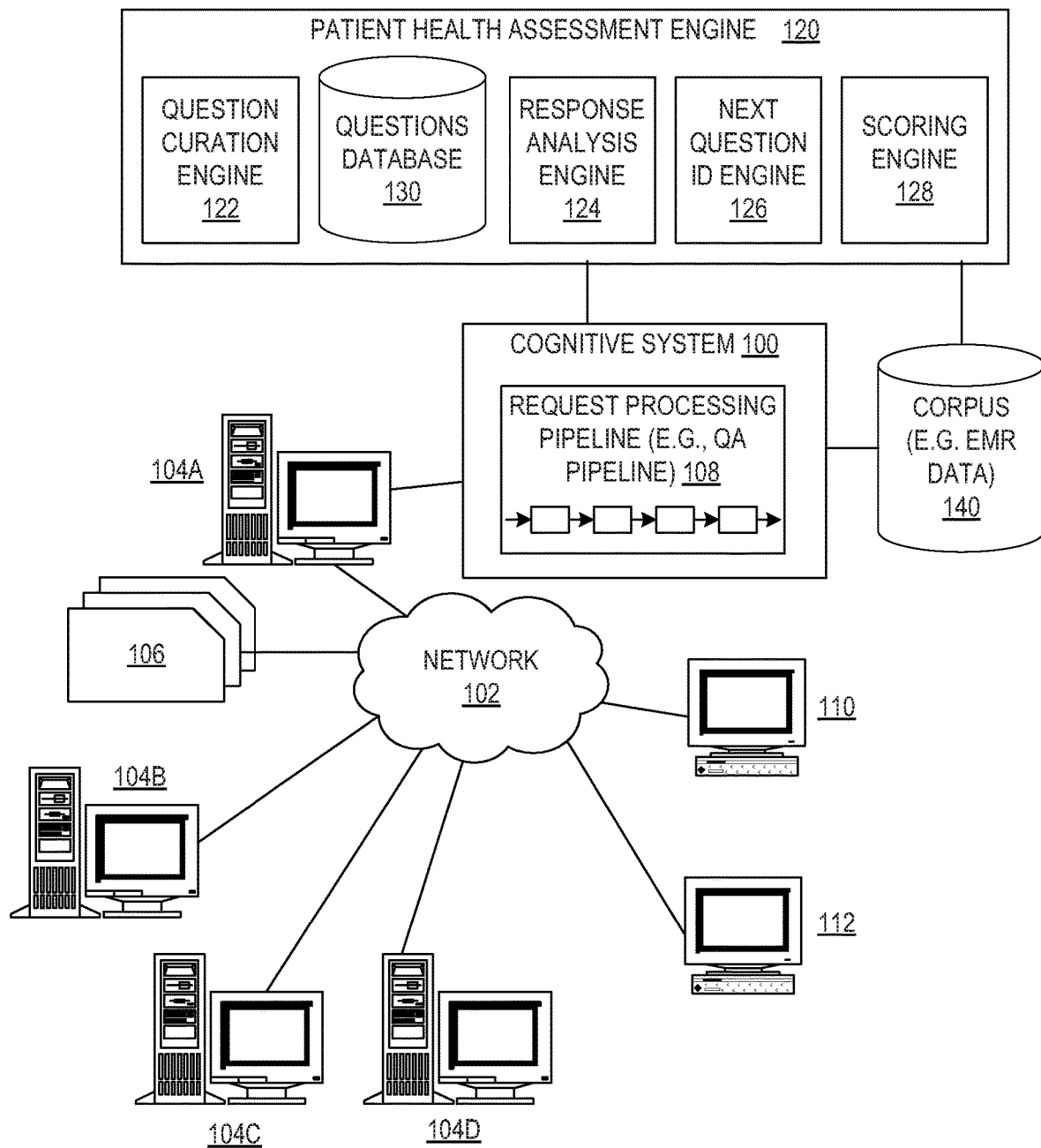
FIG. 1 depicts a schematic diagram of one illustrative embodiment of a cognitive system in a computer network.

The illustrative embodiments provide mechanisms for adaptively and dynamically generating a personalized questionnaire for health risk assessment of a patient. In the healthcare industry, conventional approach for collecting health information and medical history from patients often involves administering lengthy standard questionnaires. These standard questionnaires seek information on sociodemographic, life-style, and medical history with the aim to facilitate care providers in assessing health risks and determining feasible treatment options for patients. However, answering a lengthy list of standard questions is time-consuming and some of the information obtained may not necessarily add value to an assessment.

The proposed invention offers a technical framework to adaptively and dynamically tailor a health-risk questionnaire by integrating segmentation technologies with predictive analytic algorithms to offer a shortest, most relevant, and intuitive set of questions to a patient, which allows an accurate assessment of health risk to the patient. This invention helps solve the problem of presenting questionnaires that seek standard information may not necessarily add value to an assessment of a patient.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the illustrative embodiments provide mechanisms for adaptively and dynamically generating a personalized questionnaire for a health risk assessment of a patient. The mechanisms provide an efficient way to gather the most concise set of data required in order to conduct a health risk assessment for a given patient. The strategy offers the following advantages distinct from currently known technologies, such as:

i. Maximizing risk prediction accuracy: The mechanisms focus on predicting potential health risk of patients. The selection of questions is therefore driven by maximizing risk prediction accuracy. Specifically, questions selection criteria and priority are based on the relative importance of a question in maximizing predictive power.

ii. Leverage on exogenous data sources: With the abundance of data, the mechanisms have the capability to integrate external data sources to augment information availability and strengthen prediction power. For example, relevant data may be pulled from proprietary sources (e.g. a patient's electronic medical records (EMRs)) or open data sources (e.g. living conditions data from the United States Census Bureau). By leveraging on exogenous data, the questions that need to be asked of the patients may be reduced.

iii. Semantic and contextual relevance: To enhance quality of response, questions' arrangement is critical. A more coherent questionnaire often yields a better response. Therefore, in addition to selecting questions based on predictive power, another unique element of the mechanism is to take questions semantics into account with contextually relevant questions grouped together.

iv. Probabilistic scoring with confidence level: Existing testing and assessment tools provide only a single score. Thus, in addition to a score which indicates the likelihood of patient's risk, the mechanisms also provide an uncertainty bound to offer the confidence one can have around the estimates. The major strength of feature is that it allows patients and care providers to determine how much they could "trust" the score. Generally, the more questions the patient answers, the lower the uncertainty. This will also serve as a way to incentivize patient to complete more question.

v. Adaptable to different health risk assessment: The mechanisms may be easily adapted to different risk assessment.

Figure 2:
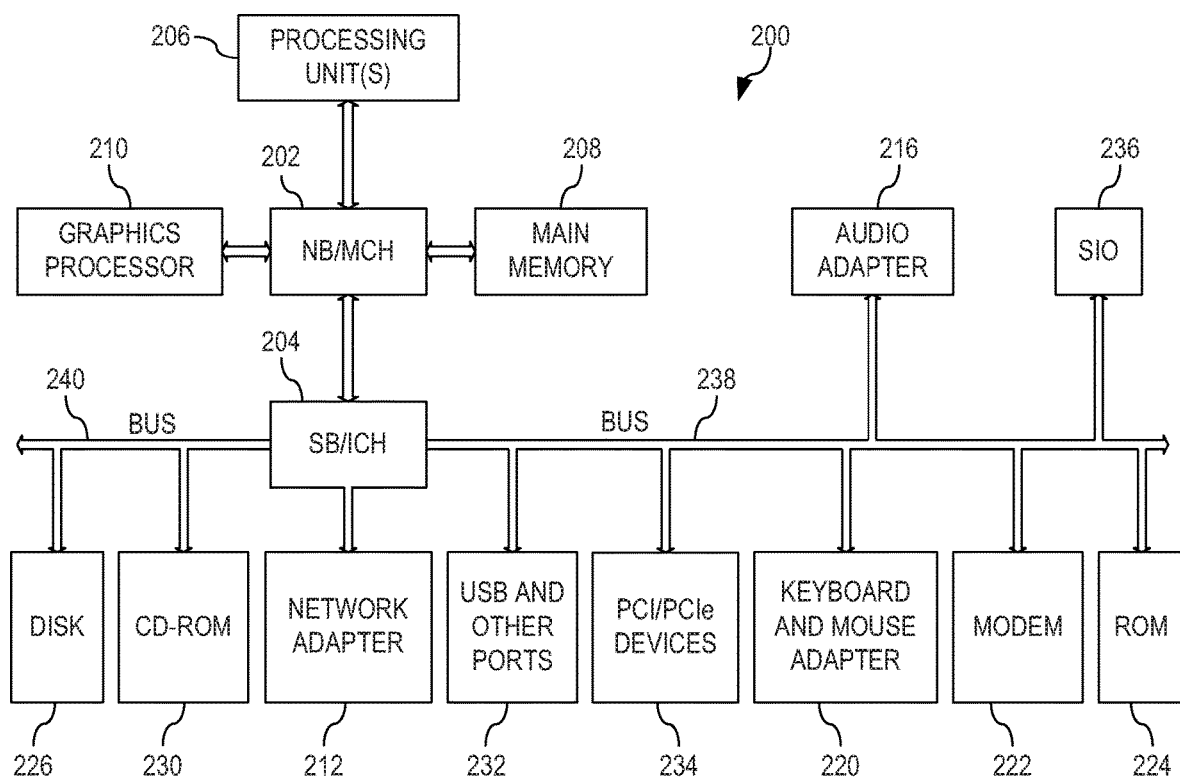
FIG. 2 is a block diagram of an example data processing system in which aspects of the illustrative embodiments are implemented.
Figure 3:
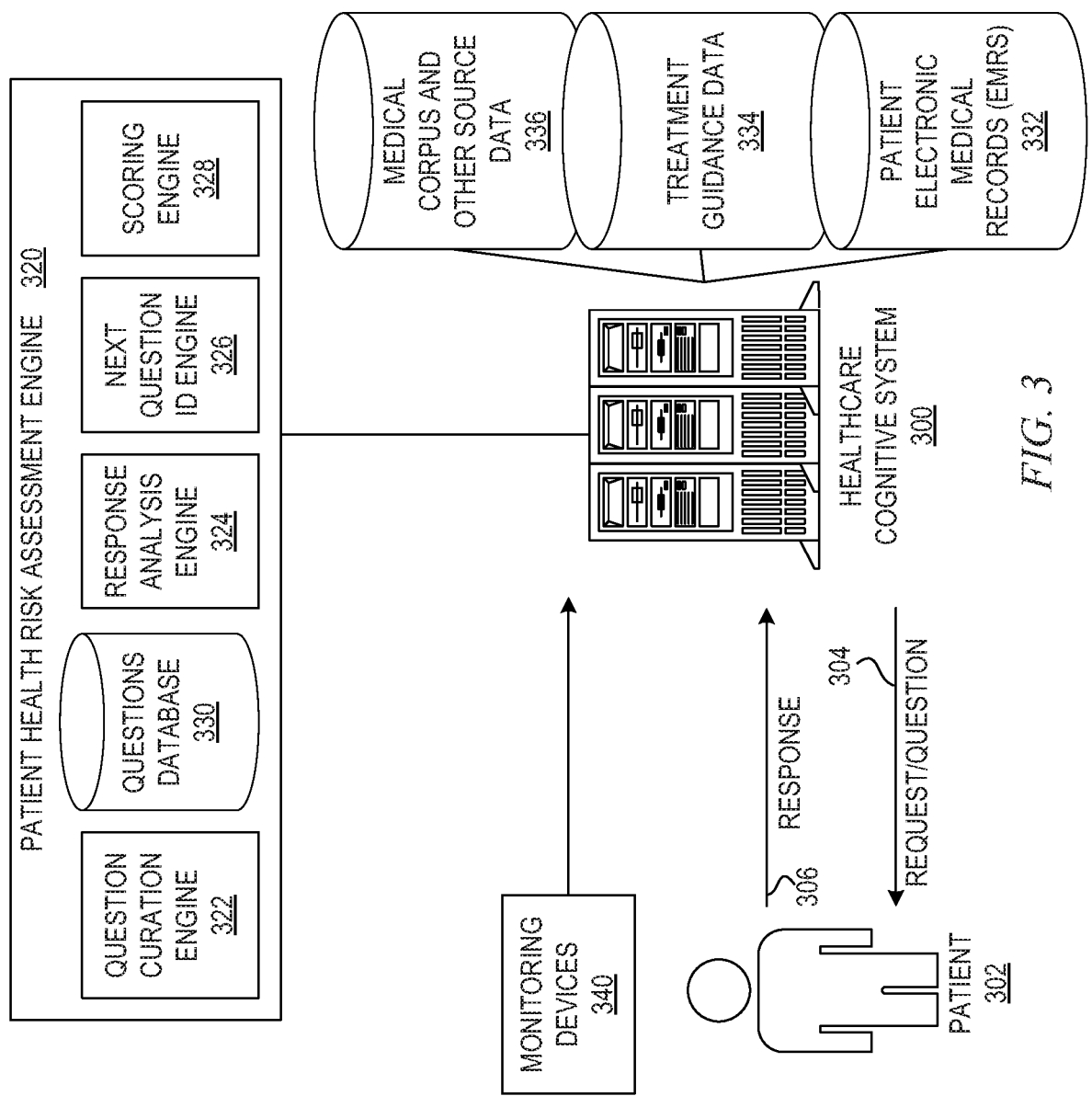
FIG. 3 is an example diagram illustrating an interaction of elements of a healthcare cognitive system in accordance with one illustrative embodiment.

Thus, the illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for adaptively and dynamically generating a personalized questionnaire for health risk assessment of a patient which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the cognitive system. As described in more detail hereafter, the particular application that is implemented in the cognitive system of the present invention is an application for adaptively and dynamically generating a personalized questionnaire for health risk assessment of a patient.

It should be appreciated that the cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a questionnaire for a particular patient. When a patient begins a questionnaire for a health risk assessment, the mechanisms of the illustrative embodiments prompt the patient with basic questions and or information, such as, for example: age, height, weight, race, sex, or the like as well as biometric information associated with a patient. The mechanisms then analyze the responses to these basic questions to group the patient to an initial patient group. That is, the mechanisms utilize a question database, which is curated utilizing historical patient data for a plurality of patients and comprises a plethora of assessment questions for determining patient risks. The question database is segmented based on patient groups. The segmentations are developed based on clustering and machining algorithms in which a unique minimal set of features were identified and ranked for each group. The selection and ranking of features is determined by various factors including the importance of the feature in providing high predictive power, its correlation with other features, semantic/contextual connection with other features, probability of obtaining high quality response (as opposed to missing value), or the like.

Once the initial grouping is established, the mechanisms request additional information (i.e. symptoms) as to why the patient is requesting service, such as, for example, chest pain, abdominal issues, forearm pain, or other condition for which the patient is present at the medical facility, which may a doctor's office, emergency facility, hospital, or the like. The mechanisms utilize the addition information to establish a next question to present to the patient. For example, if a patient is a female in her late 60s with abdominal issue, then the mechanisms may select a next question relating to gastrointestinal diseases. However, if the patient is a female in her early 20s with abdominal issues, then the mechanism may select a next question relating to pregnancy. The mechanisms adaptively and dynamically generate each next personalized question from the questions database based on the patient's prior response, asking only those pertinent questions needed to identify the health risk associated with the particular patient. The mechanisms automatically terminate the questionnaire for a health risk assessment when adequate information, as determined by the algorithm, is collected. That is, if a female patient in her 20s identifies a broken forearm, there is no need to obtain information with regard to a possible pregnancy or gastrointestinal diseases. Once the mechanisms determine that an adequate amount of information, as determined by the algorithm, has been collected, the mechanisms perform a scoring of possible health risks associated with the patient along with uncertainty level based on all responses. The mechanisms then present the gathered information along with the scoring of possible health risks and uncertainty level to a health advisor for medical treatment of the patient. The gathered information, scoring of possible health risks and uncertainty level may be utilized in many different ways, such as triaging a patient in an emergency room environment, prioritizing an order for patients to be seen by a doctor, or the like.

Each request processing pipeline used in patient health risk assessment may have its own associated corpus or corpora that they ingest and operate on, e.g., one corpus for patient electronic medical records (EMRs), another corpus for doctors, surgeons, nurses, therapists, or the like, and yet another corpus for medications related documents in the above examples. In some cases, the request processing pipelines may each operate on the same domain of input questions but may have different configurations, e.g., different annotators or differently trained annotators, such that different analysis and potential answers are generated. The cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to adaptively and dynamically generating a personalized questionnaire for health risk assessment of a patient.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence Initiate outputs to other devices base on determined details In one aspect, cognitive systems provide mechanisms for answering or responding to questions or input posed to these cognitive systems using a Question Answering pipeline or system (QA system) and/or process requests which may or may not be posed as natural language questions. The QA pipeline or system is an artificial intelligence application executing on data processing hardware that answers or responds to input pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions and/or information to cognitive system which implements the QA pipeline. The QA pipeline then determines answers or appropriate responses using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided to the input. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives input, parses the input to extract the major features of the input, uses the extracted features to formulate queries, and then applies those queries to the corpus of data. Based on the application of the queries to the corpus of data, the QA pipeline generates a set of hypotheses, or candidate answers or responses to the input, by looking across the corpus of data for portions of the corpus of data that have some potential for containing a valuable response to the input. The QA pipeline then performs deep analysis on the language of the input and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response is inferred by the input. This process is repeated for each of the responses until the QA pipeline identifies one or more responses that surface as being significantly stronger than others and thus, generates a final response, or ranked set of responses, for the input.

As mentioned above, QA pipeline mechanisms operate by accessing information from a corpus of data or information (also referred to as a corpus of content), analyzing it, and then generating responses results based on the analysis of this data. Accessing information from a corpus of data typically includes: a database query that responds to input about what is in a collection of structured records, and a search that delivers a collection of document links in response to a query against a collection of unstructured data (text, markup language, etc.). Conventional QA systems are capable of generating responses based on the corpus of data and the input, verifying responses to a collection of input for the corpus of data, correcting errors in digital text using a corpus of data, and selecting one or more responses to the input from a pool of potential responses.

Content creators, such as article authors, electronic document creators, web page authors, document database creators, and the like, determine use cases for products, solutions, and services described in such content before writing their content. Consequently, the content creators know what input the content is intended to respond in a particular topic addressed by the content. Categorizing the input, such as in terms of roles, types of information, tasks, or the like, associated with the input, in each document of a corpus of data allows the QA pipeline to more quickly and efficiently identify documents containing content related to a specific query. The content may also respond to other input that the content creator did not contemplate that may be useful to content users. The input and responses may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these input and response attributes of the content.

Operating on such content, the QA pipeline generates answers or responses for input using a plurality of intensive analysis mechanisms which evaluate the content to identify the most probable answers or responses for the input. The most probable responses are output as a ranked listing of candidate responses ranked according to their relative scores or confidence measures calculated during evaluation of the candidate responses, as a single final response having a highest ranking score or confidence measure, or which is a best match to the input, or a combination of ranked listing and final answer or response.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input information, questions, or the like. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input, such as, in accordance with the illustrative embodiments, health monitors. In one embodiment, some or all of the inputs to the cognitive system 100 are routed through the network 102. The various computing devices 104A-D on the network 102 include access points for content creators and cognitive system users. Some of the computing devices 104A-D includes devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and being a health risk assessment that is processed based on the content in the corpus or corpora of data 106. In one embodiment, the questions/requests presented to a patient are formed using natural language. The cognitive system 100 parses and interprets responses to the questions/requests via request processing pipeline 108, and provides a next questions to the cognitive system user, e.g., cognitive system user 110, containing one or more next questions, results of processing the responses provided by the patient, or the like. In some embodiments, the cognitive system 100 provides next question(s) to the patient in a ranked list while, in later illustrative embodiments, the cognitive system 100 provides a final health risk assessment determination in the form of a ranked listing of possible health conditions.

The cognitive system 100 implements request processing pipeline 108 which comprises a plurality of stages for processing an input question/request based on information obtained from the corpus or corpora of data 106. Request processing pipeline 108 generates a next question or request based on the processing of initial input information or prior response to a question/request and information derived from the corpus or corpora of data 106. In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the input information or response, which in turn are then used to formulate queries that are applied to the corpus or corpora of data 106. Based on the application of the queries to the corpus or corpora of data 106, a set of hypotheses or candidate next questions based in the input information/responses are generated by looking across the corpus or corpora of data 106 for portions of the corpus or corpora of data 106 (hereafter referred to simply as the corpus 106) that have some potential for containing a valuable response to the input information/responses. Request processing pipeline 108 of the IBM Watson™ cognitive system then performs deep analysis on the language of the input information/responses and the language used in each of the portions of the corpus 106 found during the application of the queries using a variety of reasoning algorithms.

The scores obtained from the various reasoning algorithms are then weighted against a statistical model that summarizes a level of confidence that request processing pipeline 108 of the IBM Watson™ cognitive system 100, in this example, has regarding the evidence that the potential candidate next question(s) is inferred by input information/responses. This process is be repeated for each of the candidate next question(s) to generate ranked listing of candidate next question(s) which may then be presented to the patient that submitted the input information/responses, e.g., a user of client computing device 110, or from which a final answer is selected and presented to the patient. More information about request processing pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language input information/responses, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient electronic medical records (EMRs), medical guidance documentation from one or more corpora, and the like, to provide a healthcare oriented cognitive system result.

In the context of the present invention, cognitive system 100 may provide a cognitive functionality for adaptively and dynamically generating a personalized questionnaire for health risk assessment of a patient. For example, depending upon the particular implementation, the healthcare cognitive system based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a healthcare cognitive system for adaptively and dynamically generating a personalized questionnaire for health risk assessment of a patient.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing patient health risk assessment engine 120 that for adaptively and dynamically generates a personalized questionnaire for health risk assessment of a patient. As shown in FIG. 1, patient health risk assessment engine 120 comprises question curation engine 122, response analysis engine 124, next question identification engine 126, scoring engine 128.

In the initialization of patient health risk assessment engine 120, question curation engine 122 curates questions database 130 with relevant health risk assessment questions for determining health risks utilizing historical patient data, such as patient diagnostics, medical treatment recommendation systems, medical practice management systems, personal patient care plan generation and monitoring systems, patient electronic medical records (EMR), or the like, stored within the corpus or corpora of data 106. Question curation engine 122 segments the question database based on patient groups. Question curation engine 122 develops the segmentations based on identifying unique minimal sets of features. Question curation engine 122 then, for each group, ranks the questions within each group using various factors including the importance of the feature in providing high predictive power, its correlation with other features, semantic/contextual connection with other features, a probability of obtaining high quality response (as opposed to missing value), or the like.

With the generation of questions database 130, when a patient initiates a health risk assessment with cognitive system 100, initial basic information requests and/or questions is presented to the patient. The initial basic information requests and/or questions may include, but are not limited to, age, height, weight, race, sex, or the like, biometric information associated with a patient, as well as additional information (i.e. symptoms) as to why the patient is requesting service, such as, for example, chest pain, abdominal issues, forearm pain, or other condition for which the patient is present at the medical facility, which may a doctor's office, emergency facility, hospital, or the like. Utilizing the initial information, response analysis engine 124 analyzes the information and groups the patient to an initial group that matches the patient to a most similar patient group.

With the identified initial group, next question identification engine 126 utilizes the identified group to determine a next question from questions database 130 to present to the patient, which is then presented to the patient. Based on the response to the next question, response analysis engine 124 analyzes the response information and groups the patient to a next group that matches the patient to a most similar patient group and next question identification engine 126 utilizes the identified next group to determine a next question from questions database 130 to present to the patient. This process is repeated by response analysis engine 124 and next question identification engine 126 to identify the next most relevant and predictive question people similar to the patient are likely to provide quality response.

Once response analysis engine 124 has identified a last group in a line of groups identified for assessing the health risk assessment of the patient and next question identification engine 126 has presented a last question, scoring engine 128 perform a scoring of possible health risks associated with the patient along with uncertainty level based on all responses. That is, scoring engine 128 generates a set of hypotheses, or candidate health risk conditions, by looking across the questions presented to the patient and the responses provided by the patient. Scoring engine 128 performs deep analysis on the language of the questions and responses used during the personalized questionnaire. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input information, responses, and questions. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input information, responses, and questions based on the specific area of focus of that reasoning algorithm. Each resulting score is then weighted against a statistical model. The statistical model captures how well the reasoning algorithm performed at establishing the inference between two similar passages for a particular domain during the training period of scoring engine 128. The statistical model is used to summarize a level of confidence that scoring engine 128 has regarding the evidence that the potential response, i.e. candidate questions, is inferred by the input information and responses. This process is repeated for each of the candidate health condition until scoring engine 128 identifies candidate health conditions that surface as being significantly stronger than others and thus, generates a final possible health risk, or ranked set of possible health risks, for the responses along with an uncertainty level, i.e. how confident scoring engine 128 is of the final possible health risk or ranked set of possible health risks based on the scoring. Finally, scoring engine 128 presents the final possible health risk or ranked set of possible health risks to the patient and/or medical staff for use in, for example, triaging a patient in an emergency room environment, prioritizing an order for patients to be seen by a doctor, or the like.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and request processing pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300, which may be a healthcare cognitive system such as healthcare cognitive system 100 described in FIG. 1, that is configured to adaptively and dynamically generating a personalized questionnaire for health risk assessment of a patient. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 as a human figure, the interactions with and between patient may be performed using computing devices, medical equipment, and/or the like, such that entity 302 may in fact be a computing device. For example, the interactions 304 and 306 from patient 302 may be performed orally, e.g., a doctor interviewing a patient, and may involve the use of one or more medical instruments, monitoring devices, or the like, to collect information that may be input to the healthcare cognitive system 300. That is, healthcare cognitive system 300 may receive biometric information associated with a patient from monitoring devices 340, such as blood pressure monitors, pulse oximeter, or the like.

As shown in FIG. 3, in accordance with one illustrative embodiment, a patient 302 and/or monitoring device 340 presents information to healthcare cognitive system 300 and, more specifically patient health risk assessment engine 320 within healthcare cognitive system 300. The information presented by patient 302 is based patient 302 initiating a health risk assessment with cognitive system 300, where patient health risk assessment engine 320 presents' initial basic information requests and/or questions 304 to patient 302. The initial basic information requests and/or questions 304 may include, but are not limited to, age, height, weight, race, sex, or the like, as well as additional information (i.e. symptoms) as to why the patient is requesting service, such as, for example, chest pain, abdominal issues, forearm pain, or other condition for which the patient is present at the medical facility, which may a doctor's office, emergency facility, hospital, or the like. Responsive to these basic information requests and/or questions 304, patient 302 provides responses 306 to patient health risk assessment engine 320. Additionally, if a monitoring device 340 is provided to patient 302 at the same time the initial basic information requests and/or questions 304 are initialized, monitoring device 340 may present biometric information associated with a patient to patient health risk assessment engine 320.

Upon receiving the responses from patient 302 and/or monitoring device 340, response analysis engine 324 analyzes the information and group's patient 302 to an initial group that matches patient 302 to a most similar patient group. The patient grouping are based on, but not limited to, one or more of age, height, weight, race, sex, medical conditions, symptoms, or the like. With the identified initial group, next question identification engine 326 utilizes the identified group to determine a next question from questions database 330 to present to patient 302. Questions database 330 is a database of questions generated by question curation engine 122 curating relevant health risk assessment questions for determining health risks utilizing historical patient data, such as patient diagnostics, medical treatment recommendation systems, medical practice management systems, personal patient care plan generation and monitoring systems, patient electronic medical records (EMR), or the like, stored in medical corpus and other source data 336, treatment guidance data 334, and patient EMRs 332. Question curation engine 322 segments the question database based on patient groups. Question curation engine 322 develops the segmentations based on identifying unique minimal sets of features. Question curation engine 122 then, for each group, ranks the questions within each group using various factors including the importance of the feature in providing high predictive power, its correlation with other features, semantic/contextual connection with other features, a probability of obtaining high quality response (as opposed to missing value), or the like.

Based on response 306 to next question 304, response analysis engine 324 analyzes response 306 information and groups patient 302 to a next group that matches patient 302 to a most similar patient group and next question identification engine 326 utilizes the identified next group to determine a next question 304 from questions database 330 to present to patient 302. This process is repeated by response analysis engine 324 and next question identification engine 326 to identify the next most relevant and predictive question 304 people similar to patient 302 are likely to provide quality response.

Once response analysis engine 324 has identified a last group in a line of groups identified for assessing the health risk assessment of patient 302, scoring engine 328 perform a scoring of possible health risks associated with patient 302 along with uncertainty level based on all responses 306. That is, scoring engine 328 generates a set of hypotheses, or candidate health risk conditions, by looking across the questions presented to patient 302 and responses 306 provided by patient 302. Scoring engine 328 performs deep analysis on the language of questions 304 and responses 306 used during the personalized questionnaire. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of input information/responses 306 and questions 304. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input information, responses, and questions based on the specific area of focus of that reasoning algorithm. Each resulting score is then weighted against a statistical model. The statistical model captures how well the reasoning algorithm performed at establishing the inference between two similar passages for a particular domain during the training period of scoring engine 328. The statistical model is used to summarize a level of confidence that scoring engine 328 has regarding the evidence that the potential response, i.e. candidate questions 304, is inferred by the input information and responses 306. This process is repeated for each of the candidate health condition until scoring engine 328 identifies candidate health conditions that surface as being significantly stronger than others and thus, generates a final possible health risk, or ranked set of possible health risks, for the responses along with an uncertainty level, i.e. how confident scoring engine 328 is of the final possible health risk or ranked set of possible health risks based on the scoring. Finally, scoring engine 328 presents the final possible health risk or ranked set of possible health risk to the patient and/or medical staff for use in, for example, triaging a patient in an emergency room environment, prioritizing an order for patients to be seen by a doctor, or the like.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the patient's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
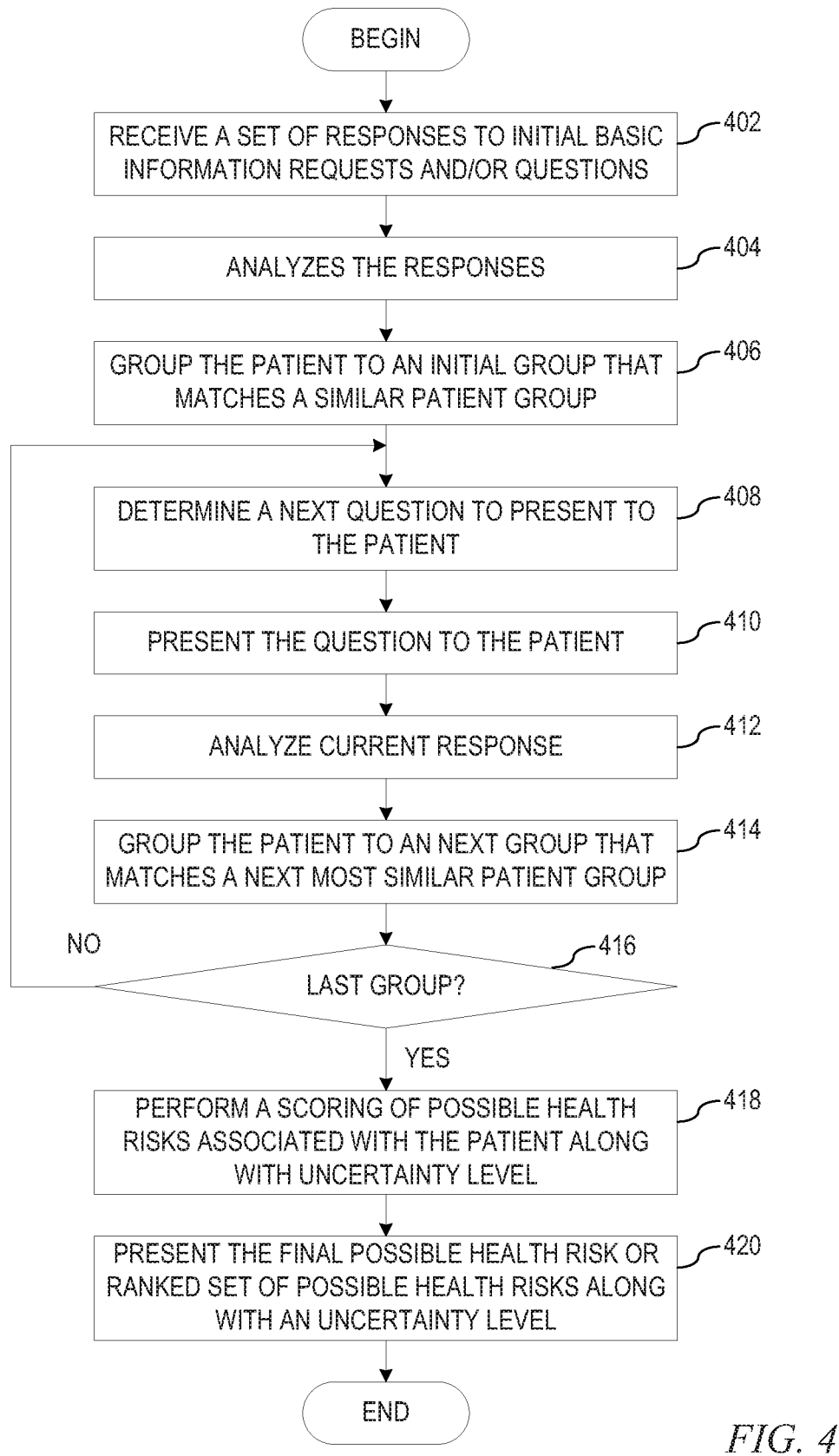
FIG. 4 is a flowchart outlining an example operation for adaptively and dynamically generating a personalized questionnaire for health risk assessment of a patient using a cognitively integrated system in accordance with one illustrative embodiment.

FIG. 4 is a flowchart outlining an example operation for adaptively and dynamically generating a personalized questionnaire for health risk assessment of a patient using a cognitively integrated system in accordance with one illustrative embodiment. The operation outlined in FIG. 4 may be implemented, for example, by a patient care analysis engine implemented in association with a healthcare cognitive system in one or more computing devices, such as patient care analysis engine 120 in FIG. 1 or patient care analysis engine 320 in FIG. 3, for example.

As the operation begins, the patient health risk assessment engine receives a set of responses to initial basic information requests and/or questions (step 402). Upon receiving the responses from patient and/or monitoring device associated with the patient, the patient health risk assessment engine analyzes the responses (step 404) and groups the patient to an initial group that matches a similar patient group (step 406). With the identified initial group, the patient health risk assessment engine utilizes the identified group to determine a next question from a questions database to present to the patient (step 408). The patient health risk assessment engine then presents the question to the patient (step 410). Based on the patient's response the next question, the patient health risk assessment engine analyzes the current response (step 412) and groups the patient to an next group that matches a next most similar patient group (step 414). The patient health risk assessment engine then determines whether the current next group is a last group (step 416).

If the patient health risk assessment engine determines that the current next group is not the last group, the operation returns to step 408. If however, the patient health risk assessment engine determines that the current next group is the last group, the patient health risk assessment engine performs a scoring of possible health risks associated with the patient along with uncertainty level based on all responses and groups (step 418). The patient health risk assessment engine then presents the final possible health risk or ranked set of possible health risks along with an uncertainty level, i.e. how confident the patient health risk assessment engine is of the final possible health risk or ranked set of possible health risks based on the scoring (step 420) to the patient and/or medical staff for use in, for example, triaging a patient in an emergency room environment, prioritizing an order for patients to be seen by a doctor, or the like. The operation terminates thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for adaptively and dynamically generating a personalized questionnaire for health risk assessment of a patient. The mechanisms offers a technical framework to adaptively and dynamically tailor a health-risk questionnaire by integrating segmentation technologies with predictive analytic algorithms to offer a shortest, most relevant, and intuitive set of questions to a patient, which allows an accurate assessment of health risk to the patient. This mechanisms helps solve the problem of presenting questionnaires that seek standard information may not necessarily add value to an assessment of a patient.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer program product comprising a computer readable storage medium having a computer readable program stored therein, wherein the computer readable program, when executed on a computing device, causes the computing device to implement a health risk assessment system for adaptively and dynamically generating a personalized questionnaire for health risk assessment of a patient and to:
   train the health risk assessment system to adaptively and dynamically generate the personalized questionnaire for the health risk assessment of the patient by executing machine learning logic that trains one or more request processing pipelines to process requests associated with different domains having differently trained annotators such that the health risk assessment mechanism operates to:
   responsive to receiving a set of responses from patient regarding age, height, weight, race, sex, medical conditions, and symptoms, as well as one or more readings from a monitoring device monitoring the patient, analyze the set of responses and the one or more readings using computer-executed natural language parsing in order to group the patient into an initial patient group from a plurality of patient groups that matches with the age, the height, the weight, the race, the sex, the medical conditions, the symptoms, and the one or more readings from the monitoring device monitoring the patient, wherein each group in the set of plurality of groups is segmented using clustering and machining algorithms in which a unique minimal set of features are identified and ranked for each group;
   utilize the initial patient group to determine an initial question from a questions database to present to the patient;
   responsive to presenting the initial question to the patient and receiving a current response from the patient, analyze the current response using natural language parsing, group the patient to a next patient group from the plurality of patient groups that matches a next most similar patient group, and identify a next question from the questions database to present to the patient;
   present each of a set of next questions to the patient one by one until a last patient group is reached, wherein, responsive to receiving a response to each next question in the set of next questions includes analyzing the response using natural language parsing, grouping the patient to the next patient group that matches the next most similar patient group, and identifying the next question from the set of questions;
   responsive to the last patient group being reached, perform a scoring of possible health risks associated with the patient based on each response provided by the patient and identified patient groupings; and
   present the final possible health risk or ranked set of possible health risks based on the scoring to one or more of the patient or a health care professional.

2. The computer program product of claim 1, wherein the initial patient group is based on a biometric reading received from the monitoring device associated with the patient.

3. The computer program product of claim 1, wherein the computer readable program further causes the computing device to:

calculate an uncertainty level value associated with the final possible health risk or ranked set of possible health risks; and present the uncertainty level to one or more of the patient or the health care professional.

4. The computer program product of claim 1, wherein the questions database is generated by the computer readable program further causing the computing device to:

curate relevant health risk assessment questions for determining health risks utilizing historical patient data;

segment the question database based on identifying unique minimal sets of features thereby forming a set of question groups; and for each question group, rank the questions within each group using various factors based on one or more an importance of the feature in providing high predictive power, a correlation with other features, semantic/contextual connection with other features, or a probability of obtaining high quality response from a patient.

5. The computer program product of claim 4, wherein the historical patient data is identified from one or more of patient diagnostics, medical treatment recommendation systems, medical practice management systems, personal patient care plan generation and monitoring systems, or patient electronic medical records (EMR).

6. The computer program product of claim 1, wherein the computer readable program to perform the scoring of possible health risks associated with the patient further causes the computing device to:

generate a set of health risk conditions using questions presented to patient and responses provided by patient;

perform deep analysis on a language of questions and responses using one or more reasoning algorithms to form a score for each health risk condition;

weight each score against a statistical model; and generate a final possible health risk or ranked set of possible health risks for the health risk assessment based on the weighted scores.

7. An apparatus comprising:

a processor; and a memory coupled to the processor, wherein the memory comprises instructions which, when executed by the processor, cause the processor to implement a health risk assessment system for adaptively and dynamically generating a personalized questionnaire for health risk assessment of a patient and to:

train the health risk assessment system to adaptively and dynamically generate the personalized questionnaire for the health risk assessment of the patient by executing machine learning logic that trains one or more request processing pipelines to process requests associated with different domains having differently trained annotators such that the health risk assessment mechanism operates to:

responsive to receiving a set of responses from patient regarding age, height, weight, race, sex, medical conditions, and symptoms, as well as one or more readings from a monitoring device monitoring the patient, analyze the set of responses and the one or more readings using computer-executed natural language parsing in order to group the patient into an initial patient group from a plurality of patient groups that matches with the age, the height, the weight, the race, the sex, the medical conditions, the symptoms, and the one or more readings from the monitoring device monitoring the patient, wherein each group in the set of plurality of groups is segmented using clustering and machining algorithms in which a unique minimal set of features are identified and ranked for each group;

utilize the initial patient group to determine an initial question from a questions database to present to the patient;

responsive to presenting the initial question to the patient and receiving a current response from the patient, analyze the current response using natural language parsing, group the patient to a next patient group from the plurality of patient groups that matches a next most similar patient group, and identify a next question from the questions database to present to the patient;

present each of a set of next questions to the patient one by one until a last patient group is reached, wherein, responsive to receiving a response to each next question in the set of next questions includes analyzing the response using natural language parsing, grouping the patient to the next patient group that matches the next most similar patient group, and identifying the next question from the set of questions;

responsive to the last patient group being reached, perform a scoring of possible health risks associated with the patient based on each response provided by the patient and identified patient groupings; and present the final possible health risk or ranked set of possible health risks based on the scoring to one or more of the patient or a health care professional.

8. The apparatus of claim 7, wherein the initial patient group is based on a biometric reading received from the monitoring device associated with the patient.

9. The apparatus of claim 7, wherein the instructions further cause the processor to:

calculate an uncertainty level value associated with the final possible health risk or ranked set of possible health risks; and present the uncertainty level to one or more of the patient or the health care professional.

10. The apparatus of claim 7, wherein the questions database is generated by the instructions further causing the processor to:

curate relevant health risk assessment questions for determining health risks utilizing historical patient data, wherein the historical patient data is identified from one or more of patient diagnostics, medical treatment recommendation systems, medical practice management systems, personal patient care plan generation and monitoring systems, or patient electronic medical records (EMR);

segment the question database based on identifying unique minimal sets of features thereby forming a set of question groups; and for each question group, rank the questions within each group using various factors based on one or more an importance of the feature in providing high predictive power, a correlation with other features, semantic/contextual connection with other features, or a probability of obtaining high quality response from a patient.

11. The apparatus of claim 7, wherein the instructions to perform the scoring of possible health risks associated with the patient further cause the processor to:

generate a set of health risk conditions using questions presented to patient and responses provided by patient;

perform deep analysis on a language of questions and responses using one or more reasoning algorithms to form a score for each health risk condition;

weight each score against a statistical model; and generate a final possible health risk or ranked set of possible health risks for the health risk assessment based on the weighted scores.

12. The apparatus of claim 10, wherein the historical patient data is identified from one or more of patient diagnostics, medical treatment recommendation systems, medical practice management systems, personal patient care plan generation and monitoring systems, or patient electronic medical records (EMR).

* * * * *